United States Patent [19]

Schneider

[11] Patent Number: 5,219,876

[45] Date of Patent: Jun. 15, 1993

[54] SUBSTITUTED-CYANO-2-[4-(PHENYL-ETHYNYL)PHENYL]-1-1 (1H-1,2,4-TRIAZOL-1-YL)ETHANE DERIVATIVES

[75] Inventor: Rupert Schneider, Riehen, Switzerland

[73] Assignee: Sandoz Ltd., Basel, Switzerland

[21] Appl. No.: 864,372

[22] Filed: Apr. 6, 1992

Related U.S. Application Data

[63] Continuation of Ser. No. 714,400, Jun. 13, 1991, abandoned, which is a continuation of Ser. No. 577,995, Sep. 4, 1990, abandoned, which is a continuation of Ser. No. 278,065, Nov. 30, 1988, abandoned.

[51] Int. Cl.$^5$ .................. A01N 43/653; C07D 249/08
[52] U.S. Cl. ..................................... 514/383; 514/184; 548/101; 548/267.4
[58] Field of Search ................ 514/184, 383; 548/101, 548/267.4

[56] References Cited

U.S. PATENT DOCUMENTS

| | | |
|---|---|---|
| 4,366,165 | 12/1982 | Muller et al. ........................ 514/383 |
| 4,507,140 | 3/1985 | Sugawanan ............................ 71/76 |
| 4,609,668 | 9/1986 | Schaub et al. ....................... 514/383 |
| 4,664,696 | 5/1987 | Schaub ................................... 71/92 |

FOREIGN PATENT DOCUMENTS

| | | |
|---|---|---|
| 61840 | 10/1982 | European Pat. Off. . |
| 145294 | 6/1985 | European Pat. Off. . |
| 234683 | 9/1987 | European Pat. Off. . |
| 59-104367 | 6/1984 | Japan . |

*Primary Examiner*—Patricia L. Morris
*Attorney, Agent, or Firm*—Allen E. Norris

[57] ABSTRACT

The invention provides compounds of formula I

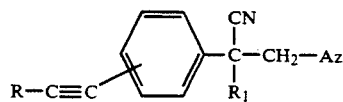

wherein R, $R_1$ and Az are as defined in the description, the fungicidal use of such compounds, compositions for facilitating such use and the preparation of compounds of formula I.

7 Claims, No Drawings

SUBSTITUTED-CYANO-2-[4-(PHENYL-ETHYNYL)PHENYL]-1-1 (1H-1,2,4-TRIAZOL-1-YL)ETHANE DERIVATIVES

This is a continuation of application Ser. No. 07/714,400, filed Jun. 13, 1991, now abandoned, which in turn is a continuation of application Ser. No. 07/577,995, filed Sep. 4, 1990, now abandoned, which in turn is a continuation of application Ser. No. 07/278,065, filed Nov. 30, 1988, now abandoned.

The present invention relates to novel 2-cyano-2-aryl-1-(azole-1-yl)-ethane derivatives, their use, compositions for facilitating their use and the preparation of novel compounds of the invention.

The invention provides compounds of formula I

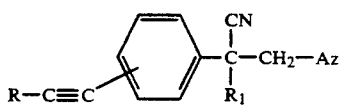

wherein
R$_1$ is C$_{1-8}$alkyl or C$_{2-8}$alkenyl unsubstituted or substituted by halogen or an heteroaromatic group; or is C$_{2-8}$alkinyl; or is C$_{3-6}$cycloalkyl-(C$_{1-3}$alkyl)$_n$ unsubstituted or substituted by C$_{1-3}$alkyl or C$_{3-6}$cycloalkyl; or is phenyl or phenyl-C$_{1-3}$alkyl unsubstituted or substituted in the phenyl ring,
n is 0 or 1,
R is H, halogen, C$_{1-5}$alkyl, R$_2$R$_3$C(OR$_4$) or unsubstituted or substituted phenyl
R$_2$ and R$_3$ independently are C$_{1-5}$alkyl,
R$_4$ is H or C$_{1-5}$alkyl and
Az is 1,2,4-triazole-1-yl or imidazole-1-yl.

The compounds of the invention contain one or more chiral centres. Such compounds are generally obtained in the form of racemic or diastereomeric mixtures. However, these and other mixtures can if desired be separated either completely or partly into the individual isomers or desired isomer mixtures by methods known in the art.

Where R is halogen, this is for example Cl, Br or I.

Where R$_1$ is phenyl or phenyl-C$_{1-3}$alkyl substituted in the phenyl ring and/or R is substituted phenyl, such phenyl is for example mono-or di-substituted by substituents selected from halogen (e.g. F, Cl, Br, I), C$_{1-5}$alkyl (e.g. CH$_3$), C$_{1-5}$alkoxy (e.g. CH$_3$O), CF$_3$, OCF$_3$, NO$_2$, OH and phenyl.

A preferred significance of R is phenyl.

Where R$_1$ is substituted C$_{3-6}$cycloalkyl-(C$_{1-3}$alkyl)$_n$, it is preferably mono- or di-substituted by C$_{1-3}$alkyl (particularly CH$_3$) in its C$_{3-6}$cycloalkyl moiety and/or by C$_{3-6}$cycloalkyl (particularly cyclopropyl) in its C$_{1-3}$alkylene moiety.

Where R and/or R$_1$ contain a C$_{1-3}$alkylene group, such alkylene group is for example CH$_2$ or CH(CH$_3$).

Where R$_1$ is optionally halogenated C$_{1-8}$alkyl, the alkyl group has preferably from 1 to 3 carbon atoms and is more preferably unsubstituted C$_{1-3}$alkyl, in particular CH$_3$ or C$_2$H$_5$.

Where R$_1$ is optionally halogenated C$_{2-8}$alkenyl or is C$_{2-8}$alkinyl it contains conveniently from 3 to 5 carbon atoms, and the double bond or triple bond is preferably not in α-position, more preferably in β-position of the carbon atom is which the CN group is bounded.

Where R$_1$ is C$_{1-8}$alkyl it is preferably C$_{1-3}$alkyl.

Where R$_1$ is C$_{2-8}$alkenyl it is preferably allyl or 1-methylallyl.

Where R$_1$ is halogen substituted C$_{1-8}$alkyl or C$_{2-8}$alkenyl, the hydrocarbon is conveniently mono-, di- or tri-substituted by halogen selected from F, Cl, Br or I.

Where R$_1$ is or contains C$_{3-6}$cycloalkyl, such cycloalkyl is preferably cyclopentyl or cyclohexyl.

Where R$_1$ is C$_{1-8}$alkyl or C$_{2-8}$alkenyl substituted by an heteroaromatic group, it is preferably heteroaryl-C$_{1-4}$alkyl or heteroaryl-C$_{2-5}$alkenyl, more preferably heteroaryl-C$_{1-3}$alkyl or heteroaryl-C$_{3-5}$alkenyl. Preferably its heteroaryl moiety is 5- or 6-membered and comprises 1 heteroatom selected from O, N or S; it is more preferably selected from pyridyl, furyl (e.g. 2-furyl) or thienyl (e.g. 2-thienyl) and is in particular 3-pyridyl.

R$_2$ and R$_3$ are preferably C$_{1-4}$alkyl, particularly, CH$_3$.

R$_4$ is preferably H or C$_{1-4}$alkyl, particularly H or CH$_3$.

Az is preferably 1,2,4-triazole-1-yl.

The R—C≡C group is preferably in the 4-position.

The compounds of formula I are obtained by
a) reacting a compound of formula II

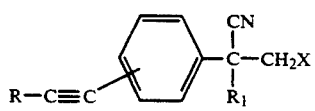

wherein
R and R$_1$ are as defined above, and
X is halogen,
with a compound of formula III

M—Az    III wherein
Az is as defined above, and
M is a metal, or
b) by reacting a compound of formula IV

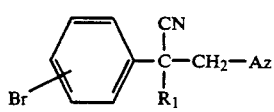

wherein
R$_1$ and Az are as defined above, with an acetylene of formula V

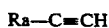

R$_a$—C≡CH    V wherein
R$_a$ is C$_{1-5}$alkyl; or is R$_2$R$_3$C(OR$_4$) as defined above or is unsubstituted or substituted phenyl; or a protective group other than the R$_2$R$_3$C(OH) group in which R$_2$ and R$_3$ are as defined above,
followed, where R$_a$ is a protective group other than said R$_2$R$_3$C(OH) group, by splitting off such protective group, or where R$_a$ is R$_2$R$_3$C(OH) by optionally splitting off such group, or
c) obtaining a compound of formula Ib

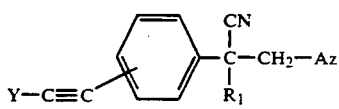

wherein
R₁ and Az are as defined above and
Y is halogen,
by substitution of the ethinyl hydrogen in a compound of formula Ic

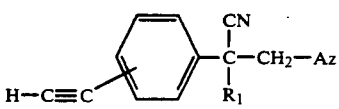

wherein
R₁ and Az are as defined above, by Y (halogen), or
d) obtaining a compound of formula Id

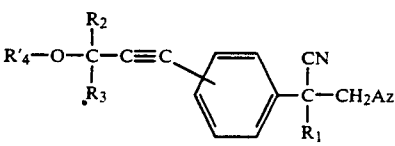

wherein
Az, R₁, R₂ and R₃ are as defined above, and
R'₄ is $C_{1-5}$alkyl,
by O-alkylating a compound of formula Ie

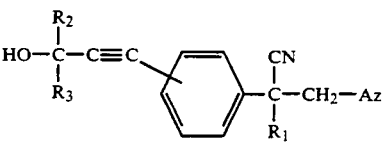

wherein
R₁, R₂, R₃ and Az are as defined above.

The reaction of a compound of formula II with a compound of formula III is conveniently effected in a suitable solvent, e.g. dimethylsulfoxide. The reaction is preferably carried out with heating, e.g. at a temperature in the range of from 100° to 150° C.

M is preferably an alkalimetal, e.g. Na.

X is preferably chlorine or bromine.

The reaction of a compound of formula IV with a compound of formula V is conveniently effected in the presence of catalytic amounts of a palladium catalyst such as bis[triphenylphosphine]-palladium dichloride or tetrakis-(triphenylposphin)-palladium(O) and copper-(I)iodide in an amine such as diethylamine, triethylamine or piperidine.

A suitable reaction temperature is between ambient temperature and reflux temperature of the reaction mixture, preferably at enhanced temperature, e.g. between 80° and 100° C.

Where the reaction is effected employing a compound of formula V wherein Ra is a protective group (e.g. the trimethylsilyl or a $R_2R_3C(OH)$ group such as the $(CH_3)_2C(OH)$ group) such group Ra may be split off employing an alkalimetalhydroxide according to known methods.

Thus the silyl group may be split off by mild treatment with dilute aqueous KOH in methanol, the $(CH_3)_2C(OH)$ group by treatment with NaOH in toluene.

The substitution of the ethinyl hydrogen in compounds of formula Ic by halogen is also effected according to processes known per se for such type of substitution reaction. It may be effected either directly, by reaction of a compound of formula Ic with a halogen cation donor such as an alkalimetal hypohalogenite (e.g. Na- or KClO), N-Cl- or N-Br-succinimide or CCl₄ (the latter under strong alkaline conditions), or via the di-Y addition product followed by the splitting off of HY from the addition product.

The etherification of a compound of formula Ie to a compound of formula Id may be effected according to methods known per se for the O-alkylation of alcohols. Suitable alkylating agents for use in this process are for example di($C_{1-5}$alkyl)sulphates, $C_{1-5}$alkyliodides or $C_{1-5}$alkylbromides.

The compounds of the invention are isolated from the reaction mixture in which they are formed by established procedures. They may be obtained in free form or in salt or metal complex form, e.g. as acid addition salt with an organic or inorganic acid such as hydrochloride, or as alcoholate e.g. as Na ethanolate, or in metal complex form, e.g. with a metal such as copper and zinc, and with anions such as chloride, sulphate and nitrate.

Compounds of formula II wherein the group R—C≡C is in the 4-position and R₁ is other than optionally substituted phenyl may e.g. be obtained by substitution of 4-bromobenzylcyanide by R₁, CH₂Br and the group R—C≡C in appropriate order, in a manner known per se, e.g. by preparing 2-cyano-2-(4-bromo-phenyl)-ethylbromide from 4-bromobenzylcyanide, substituting then the 4-bromo substituent therein by the group R—C≡C, e.g. analogous to process b) described hereinbefore, and reacting the thus obtained acetylene compound of formula VI

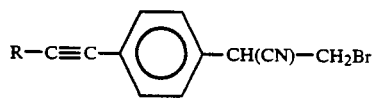

wherein
R is as defined above,
with a compound of formula VII

R'₁Br     VII wherein
R'₁ is as defined for R₁ except optionally substituted phenyl, in the presence of a phase-transfer catalyst.

Compounds of formula II wherein the group R—C≡C is in the 4-position and R₁ is optionally substituted phenyl are for example obtained by substitution in a compound of formula VIII

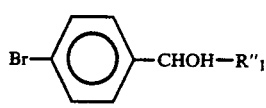

wherein
R''₁ is optionally substituted phenyl, the 4-bromo substituent by the group R—C≡C,
reacting the thus obtained compound of formula IX

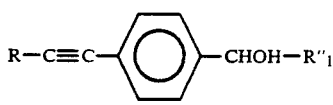

IX wherein
R and R″₁ are as defined above,
with a brominating or chlorinating agent such as PBr₃ or SOCl₂ to compounds of formula X

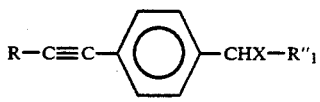

X wherein
X, R and R″₁ are as defined above,
and reacting the thus obtained compound of formula X with a metal cyanide e.g. Cu(I)CN and subsequently either directly with CH₂Br₂ or first with formaldehyde and thereafter with an halogenating agent such as PBr₃ or SOCl₂ in a manner known per se. The compounds of formula VIII may e.g. be obtained by hydrogenation of the corresponding keto compound, e.g. with NaBH₄ or by a Grignard reaction employing 4-bromobenzaldehyde as starting material.

Insofar as the production of any starting material is not particularly described, these compounds are known, or may be produced and purified in accordance with known processes, or in a manner analogous to processes described herein or to known processes.

The compounds of formula I in free form or in agriculturally acceptable salt or complex form are useful as a fungicides in the combatting of phytopathogenic fungi. Their advantageous fungicidal activity is established by in vivo tests with test concentrations from about 0.0008 to 0.05% against *Uromyces appendiculatus* (bean rust) on pole beans, against other rust fungi (such as Hemileia, Puccinia) on coffee, wheat, against *Erysiphe cichoracearum* on cucumber and against other powdery mildew fungi (*E. graminis* f.sp. *tritici*, *E. graminis* f.sp. *hordei*, *Podosphaera leucotricha*, *Uncinula necator*) on wheat, barley, apple, grape vine. Further interesting activities are i.a. observed in vitro against *Ustilago maydis* and in vivo against *Rhizoctonia solani* on cotton and in particular and in particular against Botrytis strains on beans, tomato, peperoni and grape vine. Many of the compounds of the invention have an excellent plant tolerance and a systemic action. The compounds of the invention are therefore indicated for treatment of plant, seeds and soil to combat phytopathogenic fungi, e.g. Basidiomycetes of the order Uredinales (rusts) such as Puccinia spp, Hemileia spp, Uromyces spp; Ascomycetes of the order Erysiphales (powdery mildew) such as Erysiphe spp, Podosphaera spp, and Uncinula spp; as well as Phoma; Helminthosporium; Deuteromycetes such as Pyricularia, Pellicularia (=Corticium), Thielaviopsis, Stereum spp and Botrytis.

The amount of compound of the invention to be applied, will depend on various factors such as the compound employed, the subject of the treatment (plant, soil, seed), the type of treatment (e.g. drenching, sprinkling, spraying, dusting, dressing), the purpose of the treatment (prophalactic or therapeutic), the type of fungi to be treated and the application time.

In general, satisfactory results are obtained, if the compounds of the invention are applied in an amount of from about 0.0005 to 2.0, preferably about 0.01 to 1 kg/ha, in the case of a plant or soil treatment; e.g. 0.04 to 0.500 kg of active ingredient (a.i.) per ha in crops such as cereals, or concentrations of 4 to 50 g of a.i. per hl in crops such as fruits, vineyards and vegetables (at an application volume of from 300 to 1000 l/ha—depending on the size or leaf volume of the crop—which is equivalent to an application rate of aproximately 40–500 g/h). The treatment can, if desired, be repeated, e.g. at intervals of 8 to 30 days.

The preferred compounds of formula I have an activity against Botrytis which is similar to that observed with iprodione, said compounds of formula I being also active against iprodione resistent strains.

Where the compounds of the invention are used for seed treatment, satisfactory results are in general obtained, if the compounds are used in an amount of from about 0.05 to 0.5, preferably about 0.1 to 0.3 g/kg seeds.

The term soil as used herein is intended to embrace any conventional growing medium, whether natural or artificial.

The compounds of the invention may be used in a great number of crops, such as soybean, coffee, ornamentals (i.a. pelargonium, roses), vegetables (e.g. peas, cucumber, celery, tomato and bean plants), sugarbeet, sugarcane, cotton, flax, maize (corn), vineyards, pomes and stone fruits (e.g. apple, pears, prunes) and in cereals (e.g. wheat, oats, barley, rice).

In view of their good crop tolerance many of the compounds of the invention are particularly indicated for fungicidal treatments where a favourable crop tolerance is desirable or essential, e.g. in fruit crops such as apples and grapes. Various compounds of the invention possess also a favourable curative activity.

Particularly favourable results are i.a. obtained with compounds of formula I having one or more and preferably all of the following features:

the group C≡CR is in the 4-position,
R is unsubstituted or substituted phenyl, particularly unsubstituted phenyl,
R₁ is CH₃, C₂H₅, nC₃H₇ or allyl,
Az is 1,2,4-triazol-1-yl.

The invention also provides fungicidal compositions, comprising as a fungicide a compound of the invention in free form, or in agriculturally acceptable salt or complex form in association with a agriculturally acceptable diluent (hereinafter diluent). They are obtained in conventional manner, e.g. by mixing a compound of the invention with a diluent and optionally additional ingredients, such as surfactants.

The term diluents as used herein means liquid or solid agriculturally acceptable material, which may be added to the active agent to bring it in an easier or better applicable form, resp. to dilute the active agent to a usable or desirable strength of activity. Examples of such diluents are talc, kaolin, diatomaceous earth, xylene or water.

Especially formulations used in spray form, such as water dispersable concentrates or wettable powders, may contain surfactants such as wetting and dispersing agents, e.g. the condensation product of formaldehyde with naphthalene sulphonate, an alkylarylsulphonate, a lignin sulphonate, a fatty alkyl sulphate, an ethoxylated alkylphenol and an ethoxylated fatty alcohol.

In general, the formulations include from 0.01 to 90% by weight of active agent, from 0 to 20% agriculturally acceptable surfactant and from 10 to 99.99% diluent(s). Concentrated forms of composition, e.g. emulsion concentrates, contain in general from about 2 to 90%, preferably from between 5 to 70% by weight of active agent. Application forms of formulation contain in general from 0.0005 to 10% by weight of a compound of the invention as active agent typical spray-suspensions may, for example, contain from 0.0005 to 0.05, e.g. 0,0001, 0.002 or 0.005% by weight of active agent.

In addition to the usual diluents and surfactants, the compositions of the invention may comprise further additives with special purposes, e.g. stabilizers, desactivators (for solid formulations or carriers with an active surface), agents for improving the adhesion to plants, corrosion inhibitors, anti-foaming agents and colorants. Moreover, further fungicides with similar or complementary fungicidal activity, e.g. sulphur, chlorothalonil, euparen, a guanidine fungicide such as guazatine, dithiocarbamates such as mancozeb, maneb, zineb, propineb, trichloromethane sulphenylphthalimides and analoges such as captan, captafol and folpet, benzimidazoles such as carbendazim, benomy, or other beneficially-acting materials, such as insecticides may be present in the formulations.

Examples of plant fungicide formulations are as follows:

a. Wettable powder Formulation

10 Parts of a compound of the invention are mixed and milled with 4 parts of synthetic fine silica, 3 parts of sodium lauryl sulphate, 7 parts of sodium lignin sulphonate and 66 parts of finely divided kaolin and 10 parts of diatomaceous earth until the mean particle size is about 5 micron. The resulting wettable powder is diluted with water before use to a spray liquor which may be applied by foliar spray as well as by root drench application.

b. Granules

Onto 94.5 parts by weight of quartz sand in a tumbler mixer are sprayed 0.5 parts by weight of a binder (non-ionic tenside) and the whole thoroughly mixed. 5 parts by weight of a compound of the invention are then added and thorough mixing continued to obtain a granulate formulation with a particle size in the range of from 0.3 to 0.7 mm. The granules may be applied by incorporation into the soil adjacent to the plants to be treated.

c. Emulsion Concentrate

10 Parts by weight of a compound of the invention are mixed with 10 parts of weight of an emulsifier and 80 parts by weight of toluene. The concentrate is diluted with water to the desired concentration.

d. Seed Dressing

45 Parts of a compound of the invention are mixed with 1.5 parts of diamyl phenoldecaglycolether ethylene oxide adduct, 2 parts of spindle oil, 51 parts of fine talcum and 0.5 parts of colorant rhodanin R. The mixture is ground in a contraplex mill at 10,000 rpm until an average particle size of less than 20 microns is obtained. The resulting dry powder has good adherance and may be applied to seeds, e.g. by mixing for 2 to 5 minutes in a slowly turning vessel.

The following examples further illustrate the present invention. All temperatures are in centigrade. Rf values are obtained by thin layer chromatography on silica gel, unless otherwise specified.

FINAL PRODUCTS

EXAMPLE 1

2-Cyano-2-[4-(phenylethinyl)phenyl]-1-(1H-1,2,4-triazol-1-yl)-butane

A mixture of 3.1 g (0.01 mol) of 2-cyano-2-(4-bromophenyl)-1-(1H-1,2,4-triazol-1-yl)-butane, 1.6 g (0.015 mol) of phenylacetylene, 0.05 g of tetrakis-(triphenylphosphin)palladium-(0), 0.1 g of copper (I)iodide and 0.2 g triphenylphosphine in 50 ml of triethylamine are stirred for 2 hours at 90° under a blanket of nitrogen. The reaction mixture is concentrated by evaporation at the water jet and the residue stirred with 150 ml of toluene. The thus obtained solution together with a solid phase still contained therein is washed with water (3x), dried and evaporated to give an oily residue which slowly solidifies. It may be purified by recrystallisation from a mixture of petrol ether/toluene (7:3) or by column chromatography with silicagel employing methylenchlorid/methanol (98:2) as eluant.

The thus obtained title product (compound 1) has a m.p. of 127°–129°.

EXAMPLE 2

Following the procedure of Example 1 each of the compounds of Formula I listed in Table A is obtained from the corresponding 4-bromophenyl compound of formula IV and an acetylene compound of formula V (in which Ra is R).

TABLE A

| | (Compounds of formula I wherein R—C≡C is in the 4-position) | | | |
|---|---|---|---|---|
| Cmpd. | R | $R_1$ | Az | Rf/m.p. |
| 1 | phenyl | $C_2H_5$ | Tr[1] | 127–129° |
| 2.1 | phenyl | $CH_3$ | Tr | 104° |
| 2.2 | phenyl | $n-C_3H_7$ | Tr | 63° |
| 2.3 | phenyl | $n-C_4H_9$ | Tr | liquid-Rf = 0.4[3] |
| 2.4 | phenyl | $n-C_4H_9$ | Im[2] | liquid-Rf = 0.25[3] |
| 2.5 | phenyl | $n-C_5H_{11}$ | Tr | liquid-Rf = 0.45[4] |
| 2.6 | phenyl | $n-C_5H_{11}$ | Im | liquid-Rf = 0.4[4] |
| 2.7 | phenyl | $i-C_3H_7$ | Tr | 138° |
| 2.8 | phenyl | $2-C_4H_9$ | Tr | liquid-Rf = 0.3[3] |
| 2.9 | phenyl | —$CH_2$—CH=$CH_2$ | Tr | 85° |
| 2.10 | HO—C($CH_3$)$_2$ | —$CH_2$—CH=$CH_2$ | Tr | 134° |
| 2.11 | phenyl | —$CH_2$—CHCl—$CH_2$Cl | Tr | liquid-Rf = 0.35[5] |
| 2.12 | phenyl | —$CH_2$(3-pyridyl) | Tr | liquid-Rf = 0.35[6] |
| 2.13 | phenyl | —CH($CH_3$)—CH=$CH_2$ | Im | Rf = 0.25[4] |
| 2.14 | phenyl | —CH($CH_3$)—CH=$CH_2$ | Tr | Rf = 0.45[5] |
| 2.15 | phenyl | —($CH_2$)$_2$—CH=$CH_2$ | Tr | Rf = 0.3[3] |
| 2.16 | phenyl | —($CH_2$)$_3$—CH=$CH_2$ | Tr | Rf = 0.25[3] |
| 2.17 | $CH_3O$—C($CH_3$)$_2$ | —$CH_2$—CH=$CH_2$ | Tr | Rf = 0.5[5] |
| 2.18 | phenyl | —$CH_2$—(2-furyl) | Tr | Rf = 0.45[4] |
| 2.19 | phenyl | —$CH_2$—(2-thienyl) | Tr | m.p. 154° |

TABLE A-continued (Compounds of formula I wherein R—C≡C is in the 4-position)

| Cmpd. | R | R₁ | Az | Rf/m.p. |
|---|---|---|---|---|
| 2.20 | phenyl | —CH₂—(2-furyl) | Im | Rf = 0.25[7] |
| 2.21 | phenyl | —CH₂—(4-Cl-phenyl) | Im | Rf = 0.15[5] |
| 2.22 | phenyl | —CH₂—(4-Cl-phenyl) | Tr | Rf = 0.25[3] |
| 2.23 | phenyl | cyclopentyl | Tr | Rf = 0.37[3] |
| 2.24 | n-C₄H₉ | cyclopentyl | Tr | Tr Rf = 0.38[3] |
| 2.25 | phenyl | phenyl | Tr | |
| 2.26 | t-butyl | cyclopentyl | Tr | m.p. 123° |

[1] = 1,2,4-triazole-1-yl
[2] = imidazol-1-yl
[3] = employing CH₂Cl₂/CH₃OH 98:2 as eluant
[4] = employing CH₂Cl₂/CH₃OH 95:5 as eluant
[5] = employing CH₂Cl₂/CH₃OH 97:3 as eluant
[6] = employing CH₂Cl₂/CH₃OH 9:1 as eluant
[7] = employing hexane/acetone 1:1 as eluant

EXAMPLE 3

2-Cyano-2-(4-ethinylphenyl)-1-(1H-1,2,4-triazole-1-yl)-4-pentene

A mixture of 3 g (9 mmol) of 2-cyano-2-[4-(3-hydroxy-3-methyl)-but-1-in-1-yl)phenyl]-1-(1H-1,2,4-triazol-1-yl)-4-penten and 1 g of pulverized NaOH in 60 ml of toluene is heated for 2,5 hours, under reflux and a blanket of nitrogen with stirring. The reaction mixture is then evaporated completely and the residue dissolved in 200 ml of CH₂Cl₂. The solution is washed with water (3 times with 50 ml) and dried. After evaporation of the solvent a dark, sticky oil is obtained which is chromatographed on a silicagel column employing CH₂Cl₂/CH₃OH as eluant. The solvent is then evaporated to give the title compound, m.p. 64° (colourless crystals) (Compound 3).

EXAMPLE 4

2-Cyano-2-(4-bromoethinylphenyl)-1-(1H-1,2,4-triazol-1-yl)-4-pentene 0.8 g of bromine are added, at 0°, to 5 ml of 10% NaOH while stirring vigorously. After the solution has become colourless a solution of 1 g 2-cyano-2-(4-ethinylphenyl)-1-(1H-1,2,4-triazol-1-yl)-4-pentene in 3 ml of dioxane are added dropwise, at 0°, within a few minutes. The reaction mixture is then stirred for 3 hours at room temperature, poured into 100 ml of water, extracted with diethylether, the ether extract washed with water (3 times), dried and the ether evaporated. The residue is heated for 3 hours at high vacuum and a temperature of 50°-60° C. The thus obtained title compound has a Rf value of 0.75, employing CH₂Cl₂/CH₃OH 9:1 as eluant (Compound 4).

EXAMPLE 5

2-Cyano-2-[4-(phenylethinyl)phenyl]-1-(1H-1,2,4-triazol-1-yl)-butane 2.1 g (0.03 mol) triazole are dissolved in 16 ml dimethylsulfoxide, 1.2 g (0.03 mol) pulverised sodium hydroxide are added with stirring and the mixture heated to 110°. At this temperature a solution of 3.8 g (0.011 mol) 2-cyano-2-[4-(phenylethinyl)-phenyl]-butylbromide in 16 ml of dimethylsulfoxide is added dropwise and the mixture stirred for two more hours at 110°. After cooling the reaction mixture is poured into water, extracted with diethyl ether, washed with water, dried with anhydrous Na₂SO₄ and evaporated under water jet vacuum. The residue is chromatographed on a silica gel column employing CH₂Cl₂/CH₃OH 98:2 as eluant. The thus obtained oily title compound solidifies and is then recrystallised from ligroine to give colourless crystals, m.p. 129°.

EXAMPLE 6

2-Cyano-2-(4-bromophenyl)-1-(1H-1,2,4-triazol-1-yl)-3-(pyridin-3-yl)propane

Analogous to the procedure of Example 1, employing 2-cyano-2-(4-bromophenyl)-1-(pyridin-3-yl)-ethane and phenylacetylene as starting materials the title compound is obtained. Rf value 0.25 on silicagel employing CH₂Cl₂/CH₃OH 95:5 as an eluant.

The compound 2-cyano-2-(4-bromophenyl)-3-(pyridin-3-yl)propylbromide, obtained as an intermediate in the course of the reaction has an Rf value of 0.35 (on silicagel, employing CH₂Cl₂/CH₃OH 98:2 as an eluant.

EXAMPLE 7

Analogous to the procedure of Example 5, employing the corresponding compounds of formula II and formula III, the compounds listed in Table A and of Examples 3, 4 and 6 are obtained.

INTERMEDIATES

EXAMPLE 8

2-Cyano-2-(4-bromophenyl)-1-(1H-1,2,4-triazol-1-yl)-butane a) A mixture of 35 g (0.156 mol) of 2-(4-bromophenyl)-propyl-cyanide, 50 ml methylenebromide, 50 ml of 50% sodiumhydroxyde and 4 g of benzyl-triethylammoniumbromide is heated for 4 hours under reflux (95°). The reaction mixture is cooled, diluted with 200 ml of CH₂Cl₂. The organic phase is separated off and washed with water (3 times with 100 ml each). The solvent is evaporated and the residue recrystallised from hexane/diethylether 95:5 to give 2-cyano-1-(4-bromophenyl)-butyl-bromide (m.p. 87°).

b) 2.2 g (0.032 Mol ) of 1,2,4-triazole and 1.3 g (0.032 mol) pulverised NaOH in 30 ml of dimethylsulfoxide are heated at 110°. To this mixture are added, within a few minutes, at 110° a solution of 2-cyano-2-(4-bromophenyl)butylbromide in 10 mol of dimethylsulfoxide. The reaction mixture is stirred at 110° for another 90 minutes, poured into 600 ml of water and extracted several times with diethylether. The united ether phases are washed with water and dried with magnesiumsulfate. Thereafter the ether is evaporated at the water jet and residues of dimethylsulfoxide at high vacuum to give the title compound (solid; m.p. 68°-70°, Rf=0.45 employing CH₂Cl₂/CH₃OH 95:5 as eluant).

EXAMPLE 9

2-Cyano-2-(4-bromophenyl)-1-(1H-1,2,4-triazole-1-yl)-4,5-dichloropentane

A solution of 2-cyano-2-(4-bromophenyl-1-(1H-1,2,4-triazol-1-yl)-4-penten (4g; 0.0126 mol) in chloroform (30 ml) is treated with chlorine (1.42 g; 0.02 mol) while stirring and the reaction mixture stirred for another 3 hours at room temperature. The reaction solution is washed, once with 50 ml 2N NaOH and thereafter three times with 50 ml water each. The residue is chromatographed over silicagel employing $CH_2Cl_2/CH_3OH$ 95:5 to give the title compound ($Rf=0.45$).

EXAMPLE 10

2-Cyano-2-(4-bromophenyl)-1-(pyridin-3-yl)-ethan 50 g (0.26 Mol) of 4-bromobenzylcyanide and 28 g of pyridine-3-carbaldehyde in 300 ml of $CH_3OH$ are cooled to 10°. Thereto are added dropwise, within 15 minutes and with stirring, 14 ml of NaOH 10%. The mixture is stirred for 1 hour at 10° and subsequently 1 hour at room temperature, and then diluted with 500 ml of water. The precipitated solid is sucked off, dried and recrystallized in toluene.

The thus obtained 1-cyano-1-(4-bromophenyl)-2-(pyridin-3-yl)-ethene (m.p. 126°) is dissolved in 800 ml of $CH_3OH$, and then 10 g of $NaBH_4$ are added, with stirring, within 20 minutes at 20°-30°. The mixture is stirred for 12 hours at room temperature and the solvent evaporated at the water jet. The residue is suspended in 1000 ml of water, sucked off, dried and recrystallised in toluene (m.p. 111°).

EXAMPLE 11

[4-(Phenylethinyl)phenyl]-acetonitrile

A mixture of 49 g (0.25 mol) 4-bromobenzylcyanide, 30 g (0.3 mol) phenylacetylene, 0.1 g di(triphenylphosphine)-palladium(II-dichloride, 0.1 g copper(I)iodide and 0.2 g triphenylphosphine in 300 ml triethylamine are heated for 20 hours under a blanket of $N_2$ and vigorously stirred. The mixture is then evaporated under water jet vacuum, the residue heated in hexane and the undissolved solid sucked off and dried. The thus obtained title compound is employed as such in the following reaction step.

EXAMPLE 12

2-[Phenylethinyl)phenyl]-butyronitrile

To 1.8 (0.975 mol) NaH in 30 ml dimethylformamide are added dropwise, at 0° to 10°, a solution of 14 g (0.064 mol) [4-(phenylethinyl)phenyl]acetonitrile in 30 ml dimethylformamide and the mixture stirred until the $H_2$ gas development ceases.

Then are added dropwise, at 0° to 10°, 9.8 g (0.09 mol) of ethylbromide in 20 ml of dimethylformamide and the mixture is stirred for 8 more hours at room temperature. After addition of a few ml of water to destroy excessive NaH, the reaction mixture is poured into 1000 ml of water, extracted with diethyl ether, the ether extracts washed with water, dried and evaporated and the residue chromatographed over a silica gel column, employing hexane:acetone 95.5 as an eluant. The title compound has a Rf-value of 0.22 and solidifies after evaporation of the solvent (m.p. 75°).

EXAMPLE 13

2-Cyano-2-[4-(phenylethinyl)phenyl]butyl bromide

To a solution of 5 g (0.021 mol) 2-[4-(phenylethinyl)-phenyl]-butyronitrile in 65 ml $CH_2Br_2$ are added, with stirring, 64 g 50% (0.8 mol) NaOH and 5.5 g (0.025 mol) benzyltriethylammoniumchloride. The mixture is stirred for 5 hours at 95°, cooled and 250 ml $CH_2Cl_2$ are added. The organic phase is separated off, washed, dried and evaporated in vacuum. The thus obtained title compound is kept for one hour at 70°-80° under high vacuum and crystallises from toluene: ligroine 1:2, m.p. 107°.

EXAMPLE 14

3-Cyano-3-[4-bromophenyl]-2-ketopropionic acid ethyl ester

To a solution of 53 g (0.27 mol) 4-bromobenzylcyanide in 44 g (0.3 mol) oxalic aid diethyl ester are added a solution of 6.2 g (0.27 mol) sodium in 82 ml ethanol. The temperature rises slightly. The mixture is stirred for 30 minutes at 50° and stirred for another 12 hours at room temperature. The mixture is rendered light acid with the aid of sulfuric acid, the precipitate sucked off, washed with water, dried to give the title compound as a yellow powder, m.p. 146°.

EXAMPLE 15

2-Cyano-2-(4-bromophenyl)ethanol

To a mixture of 87 g (0.29 mol) 3-cyano-3-(4-bromophenyl)-2-ketopropionic acid ethyl ester, 44 ml 38% formaldehyde and 180 ml water are added dropwise within 1 hour and with stirring, at a temperature of 10°-15°, a solution of 26 g $Na_2CO_3$ in 85 ml water. The mixture is stirred further for 17 hours at room temperature and then three times extracted with 200 ml diethylether. The ether solution is washed with water, dried, evaporated and the residue kept for one hour at 60° under high vacuum. The oily residue (title compound) is chromatographed over a silica gel column with $CH_2Cl_2/CH_3OH$ 97:3, $Rf=0.4$.

EXAMPLE 16

2-Cyano-2-(4-bromophenyl)-ethylbromide

To a mixture of 24 g (0.11 mol) 2-cyano-2-(4-bromophenyl)-ethanol and 4.5 g (0.055 mol) pyridine in 100 ml $CH_2Cl_2$ are slowly added, at $-5°$ to 0°, 12 g (0.044 mol) $PBr_3$. The mixture is stirred for 3 hours at room temperature, thereafter for 2 hours at 40°, allowed to cool off, then poured into 500 ml ice water and extracted with $CH_2Cl_2$. The extract is washed with water, dried and evaporated. The resulting residue is chromatographed over a silica gel column with hexane/diethylether 6:4. The glassy residue obtained after evaporation is worked up in toluene and thereafter ether to give the title compound in the form of a yellow powder, m.p. 171° (decomposing).

I claim:

1. A compound of formula I

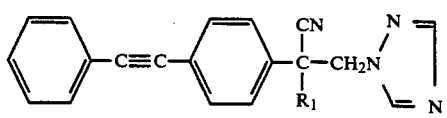

wherein $R_1$ is $C_{1-3}$alkyl or allyl, in free form, salt or metal complex form.

2. A compound according to claim 1, wherein $R_1$ is $CH_3$, $C_2H_5$ or allyl.

3. A compound according to claim 2, wherein $R_1$ is $C_2H_5$.

4. A compound according to claim 2, wherein $R_1$ is allyl.

5. A compound according to claim 2, wherein $R_1$ is $CH_3$.

6. A fungicidal composition comprising a fungicidally effective amount of a compound of formula I according to claim 1 in free form or in agriculturally acceptable salt or complex form.

7. A method of combatting phytopathogenic fungi comprising applying to such fungi or their locus a fungicidally effective amount of a compound claimed in claim 1 in free form or in agriculturally acceptable salt or complex form.

* * * * *